(12) United States Patent
Lee et al.

(10) Patent No.: US 9,593,354 B2
(45) Date of Patent: Mar. 14, 2017

(54) METHOD FOR PRODUCING L-LYSINE USING MICROORGANISMS HAVING ABILITY TO PRODUCE L-LYSINE

(71) Applicant: CJ CHEILJEDANG CORPORATION, Seoul (KR)

(72) Inventors: Kwang Ho Lee, Seoul (KR); Sang Jo Lim, Incheon (KR); Jun Ok Moon, Seoul (KR); Jae Woo Jang, Suwon-si (KR); Su Jin Park, Seoul (KR); Sang Hee Park, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 14/367,818

(22) PCT Filed: Dec. 21, 2012

(86) PCT No.: PCT/KR2012/011328
§ 371 (c)(1),
(2) Date: Jun. 20, 2014

(87) PCT Pub. No.: WO2013/095071
PCT Pub. Date: Jun. 27, 2013

(65) Prior Publication Data
US 2015/0099281 A1    Apr. 9, 2015

(30) Foreign Application Priority Data
Dec. 21, 2011   (KR) .................. 10-2011-0139527

(51) Int. Cl.
| | |
|---|---|
| C12P 13/08 | (2006.01) |
| C12N 9/12 | (2006.01) |
| C12N 9/00 | (2006.01) |
| C12N 9/10 | (2006.01) |
| C12N 15/52 | (2006.01) |
| C12N 15/74 | (2006.01) |
| C12N 15/63 | (2006.01) |

(52) U.S. Cl.
CPC ............ *C12P 13/08* (2013.01); *C12N 9/1022* (2013.01); *C12N 9/1217* (2013.01); *C12N 9/93* (2013.01); *C12N 15/52* (2013.01); *C12N 15/74* (2013.01); *C12Y 202/01001* (2013.01); *C12Y 207/02004* (2013.01); *C12Y 604/01001* (2013.01); *C12N 15/63* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,624,830 A | | 4/1997 | Mullen et al. |
| 6,221,636 B1 † | | 4/2001 | Hayakawa |
| 7,267,967 B1 * | | 9/2007 | Eikmanns ............... C12N 9/93 435/106 |
| 2003/0162269 A1 | | 8/2003 | Kreutzer et al. |
| 2007/0259408 A1 | | 11/2007 | Bathe et al. |
| 2009/0325244 A1 * | | 12/2009 | Herold ................ C12N 15/77 435/113 |
| 2013/0004999 A1 † | | 1/2013 | Reth |
| 2014/0325709 A1 | | 10/2014 | Plesch et al. |

FOREIGN PATENT DOCUMENTS

| | | |
|---|---|---|
| JP | 2011-518571 A | 6/2011 |
| KR | 102008025355 A | 3/2008 |
| KR | 1020090082702 A | 7/2009 |
| WO | 0168894 A1 † | 9/2001 |
| WO | WO0168894 * | 9/2001 |
| WO | 2009/133114 A1 | 11/2009 |
| WO | 2011/158975 A1 | 12/2011 |

OTHER PUBLICATIONS

Becker et al. (Life Sci 2010, 10, No. 5, 430-438.*
Accession AWV64596. Jul. 9, 2009.*
Accession ADC23695. Dec. 18, 2003.*
Accession AER28976. Mar. 22, 2007.*
Becker et al., "Systems level engineering of *Corynebacterium glutamicum*—Reprogramming translational efficiency for superior production," *Eng. Life Sci.* 10(5):430-438 (2010).
Jakobsen et al., "Overexpression of Wild-Type Aspartokinase Increases L-Lysine Production in the Thermotolerant Methylotrophic Bacterium *Bacillus methanolicus*," *Applied and Environmental Microbiology* 75(3):652-661 (Feb. 2009).
GENBANK Accession No. X57226 (Nov. 14, 2006).
Becker et al., "From zero to hero—Design based systems metabolic engineering of *Corynebacterium glutamicum* for $_L$-lysine production," *Metabolic Engineering* 13:159-168 (2011).
Database Accession No. AXK24447 (WO 2006/069610, SEQ:53931) (Dec. 10, 2009).
Database Accession No. AZN08069 (Dec. 8, 2011).
Database Accession No. AM747626 (Jun. 21, 2007).
Database Accession No. AWW23169 (Oct. 29, 2009).
Database Accession No. AEE27731 (Feb. 9, 2006).
Extended European Search Report dated Nov. 6, 2015, corresponding to EP Application No. EP 12 85 988.2.
Judith Becker, "From zero to hero—Design-based systems metabolic engineering of Corynebacterium glutamicum for L-lysine production" pp. 159-168, 2011, Metabolic Engineering, 13.†
Judith Becker et al., "Systems level engineering of Corynebacterium glutamicum—Reprogramming translational efficiency for superior production", pp. 430-438, 2010, Eng. Life Sci., 10, No. 5.†

(Continued)

*Primary Examiner* — Christian Fronda
(74) *Attorney, Agent, or Firm* — Seed IP Law Group LLP

(57) ABSTRACT

The present invention relates to a modified polynucleotide encoding aspartate kinase (EC:2.7.2.4; hereinafter, referred to as LysC), transketolase (EC:2.2.1.1; hereinafter, referred to as Tkt) or pyruvate carboxylase (EC:6.4.1.1; hereinafter, referred to as Pyc), in which the initiation codon is substituted with ATG, a vector including the same, a microorganism transformed with the vector, and a method for producing L-lysine using the same.

4 Claims, No Drawings

(56) References Cited

OTHER PUBLICATIONS

Judith Becker et al., "Metabolic Engineering of the Tricarboxylic Acid Cycle for Improved Lysine Production by Corynebacterium glutamicum", pp. 7866-7869, Dec. 2009, Applied and Environmental Microbiology, vol. 75, No. 24.†

Nicole Kennerknecht et al., "Metabolic Engineering: Entwicklung von Bakterienstammen fur die Lysinproducktion", pp. 582-585, 5/03, BIOspektrum.†

Masato Ikeda et al., "Molecular Analysis of the Corynebacterium glutamicum Transketolase Gene", pp. 1806-1810, 1999, Biosci. Biotechnol. Biochem., 63 (10).†

\* cited by examiner
† cited by third party

METHOD FOR PRODUCING L-LYSINE USING MICROORGANISMS HAVING ABILITY TO PRODUCE L-LYSINE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_424USPC_SEQUENCE_LISTING.txt. The text file is 20 KB, was created on Jun. 19, 2014, and is being submitted electronically via EFS-Web.

BACKGROUND OF THE INVENTION

1. Field of the Invention

The present invention relates to a modified polynucleotide, in which an initiation codon is substituted with ATG, a vector comprising the same, a microorganism comprising the polynucleotide, and a method for producing L-lysine using the same.

2. Description of the Related Art

Strains of the genus *Corynebacterium*, specifically *Corynebacterium glutamicum*, are Gram-positive microorganisms which are extensively used to produce L-lysine. L-lysine is used for animals feed, medicines and cosmetics for humans, and is produced through fermentation of the *Corynebacterium* strain.

Conventionally, a strain of the genus *Corynebacterium* having enhanced lysine biosynthesis genes and a method of producing L-lysine using the same are known. For example, U.S. Pat. No. 6,746,855 discloses a method for producing L-lysine by culturing *Corynebacterium* which has an enhanced expression of lysE gene (lysine export carrier gene), and additionally introduced genes selected from the group consisting of a dapA gene, a lysC gene, a pyc gene and a dapB gene.

Another method is to amplify genes on the lysine biosynthesis pathwayor to modify a promoter. For example, Korean Patent application laid-open Nos. 2009-0082702 and 2009-0084099 disclose a method for producing L-lysine by introducing improved promoters of ddh and lysC-asd operon into *Corynebacterium*. Korean Patent application laid-open No. 2008-0025355 discloses a method for improving lysine productivity by amplifying the copy number of the genes on the lysine biosynthesis pathway, which are aspB, lysC, asd, dapA, dapB, lysA, and pyc, in the chromosome.

Meanwhile, the initiation codon which is recognized by ribosomes to initiate translation in the chromosome is usually ATG. Translation can be controlled according to the initiation codon of the gene, and the sequence of the initiation codon is important in the regulation of protein activity. However, while ATG is the common initiation codon among the lysine biosynthesis genes derived from *Corynebacterium glutamicum*, the initiation codon of lysC and pyc genes is GTG, and TTG is for tkt gene on pentose phosphate pathway contains the initiation codon of TTG (reference: J. Biotechnol., 104: 5-25, 2003).

The present inventors have made many efforts to find a method for improving lysine productivity, and as a result, they found that the initiation codon of the wild-type lysC, tkt and pyc genes can be substituted with ATG to enhance the activities of aspartate kinase, transketolase and pyruvate carboxylase over their endogenous activities, thereby completing the present invention.

SUMMARY OF THE INVENTION

An object of the present invention is to provide a modified polynucleotide encoding aspartate kinase (EC:2.7.2.4; hereinafter, referred to as LysC), transketolase (EC:2.2.1.1; hereinafter, referred to as Tkt) or pyruvate carboxylase (EC:6.4.1.1; hereinafter, referred to as Pyc), wherein the initiation codon of the polynucleotide is substituted with ATG.

Another object of the present invention is to provide a vector comprising one or more modified polynucleotides encoding aspartate kinase, transketolase, or pyruvate carboxylase, in which the initiation codon of the polynucleotide is substituted with ATG.

Still another object of the present invention is to provide a microorganism, in which one or more the enzymes have enhanced activity compared to their endogenous activity.

Still another object of the present invention is to provide a method for producing L-lysine, comprising the steps of culturing the microorganism, and recovering L-lysine from the cultured microorganism or the culture broth.

DETAILED DESCRIPTION OF THE PREFERRED EMBODIMENTS

In one aspect, the present invention provides a modified polynucleotide encoding aspartate kinase (EC:2.7.2.4; hereinafter, referred to as LysC), transketolase (EC:2.2.1.1; hereinafter, referred to as Tkt) or pyruvate carboxylase (EC:6.4.1.1; hereinafter, referred to as Pyc), in which the initiation codon of the polynucleotide is substituted with ATG.

Each polynucleotide encoding aspartate kinase, transketolase or pyruvate carboxylase may also include a partial substitution, deletion, insertion or addition in the polynucleotide, as long as each of them has the enzymatic activity, and may have 70% or more homology, specifically 80% or more homology, more specifically 90% or more homology, and much more specifically 95% or more homology, and most specifically 100% homology based on the known polynucleotide.

As used herein, the term "homology (homologous)" means the degree of similarity between nucleotide sequences of lysC gene, tkt gene or pyc gene of the wild-type and nucleotide sequences of the corresponding modified genes thereof, that is, modified lysC gene, tkt gene or pyc gene, in which a part of the polynucleotides is substituted, deleted, inserted or added.

As used herein, the term "initiation codon" means 3 nucleotides corresponding to a translation start point when a coding sequence of mRNA (messenger RNA) is translated into a protein. In general, initiation codons found in the chromosome of microorganisms are ATG (AUG on mRNA), GTG (GUG on mRNA) and TTG (UUG on mRNA), and they exist in a ratio of 62.5%~66.5%, 23.1%~24.3% and 10.3%~13.2% according to the analysis result of the entire genome sequence of *Corynebacterium glutamicum* (reference: Handbook of *Corynebacterium glutamicum*, 40p, Lothar Eggeling & Michael Bott, 2005).

Among the lysine biosynthesis genes derived from *Corynebacterium* reported until now, lysC and pyc have the initiation codon of GTG, and tkt has the initiation codon of TTG. The initiation codon of these genes is not ATG, which is regarded as a unique characteristic of *Corynebacterium*.

The modified polynucleotide according to the present invention is characterized in that the initiation codon of the lysC, tkt or pyc gene is substituted with ATG, and these modified polynucleotides having such substituted initiation codon have been first modified by the present inventors. In more detail, GTG initiation codon of the polynucleotide encoding aspartate kinase (LysC) or pyruvate carboxylase (Pyc) is substituted with ATG, and TTG initiation codon of the polynucleotide encoding transketolase (Tkt) is substituted with ATG in the present invention. More specifically, the sequences of lysC, tkt, and pyc genes are SEQ ID NOs. 13, 14, and 15, respectively, the sequences of the genes having the substituted initiation codon as ATG are represented by SEQ ID NOs. 16, 17, and 18, respectively.

The base substitutions of the initiation codons may be performed by any method known in the art, for example, site-specific mutagenesis, homologous recombination, but is not limited thereto.

In another aspect, the present invention provides a vector comprising one or more modified polynucleotides of the modified polynucleotides encoding aspartate kinase, transketolase or pyruvate carboxylase, in which the initiation codon of the polynucleotide is substituted with ATG.

The modified polynucleotides having the substituted initiation codon as ATG and encoding aspartate kinase, transketolase or pyruvate carboxylase, which is comprised in the vector of the present invention, may include those in which a part of the polynucleotides is substituted, deleted, inserted or added, as long as they have enzymatic activity, and may have 70% or more homology, specifically 80% or more homology, more specifically 90% or more homology, much more specifically 95% or more homology, and most specifically 100% homology.

Further, the modified polynucleotides having the substituted initiation codon as ATG and encoding aspartate kinase, transketolase or pyruvate carboxylase, which is comprised in the vector of the present invention, may also include only a part of the gene encoding aspartate kinase, transketolase or pyruvate carboxylase, as long as they have the substituted initiation codon as ATG.

As used herein, the term "vector" refers to a DNA construct that contains a base sequence which is operably linked to a suitable control sequence, to expresses a target gene in a suitable host. The control sequences may include a promoter to initiate transcription, a certain operator sequence to control such transcription, a sequence encoding a suitable ribosome-binding site on the mRNA, and a sequence to control termination of transcription and translation. The vector used in the present invention is not particularly limited, and may be any vector known in the art, as long as it is replicable in the host. For example, the vector may be a plasmid, a phage particle, or a potential genome insert, and is specifically pDZ (Korean Patent No. 10-0924065), but is not limited thereto. Once transformed into a suitable host, the vector may be replicated or function independently of the host genome, or may be integrated into the genome itself.

Specifically, a nucleotide sequence (SEQ ID NO. 13, 14 or 15) comprising the initiation codon of the lysC, tkt or pyc gene was acquired, and based on this sequence, primers having the substituted initiation codon as ATG were synthesized. PCR was carried out using the primers and a chromosomal DNA of an L-lysine-producing strain as a template, so as to obtain DNA of which one end is substituted with ATG. This DNA fragment thus obtained was cloned into a vector to obtain a final recombinant vector. More specifically, in the present invention, pDZ-lysC(ATG), pDZ-tkt(ATG) and pDZ-pyc(ATG) vectors were constructed, respectively.

In still another aspect, the present invention provides a microorganism which includes one or more modified polynucleotides having the substituted initiation codon as ATG and encoding an enzymes selected from the group consisting of aspartate kinase, transketolase and pyruvate carboxylase, and then improved in translation levels of mRNAs transcribed from the polynucleotides into proteins, resulting in enhanced activities of one or more of the enzymes compared to endogenous activities thereof. The microorganism of the present invention may have enhanced activities of aspartate kinase, transketolase or pyruvate carboxylase by using the modified polynucleotides in combinations of one, two, or three thereof, in which the modified polynucleotides encode the corresponding enzymes and are substituted with ATG on initiation codon.

In order to substitute ATG for the initiation codons of the target genes on the chromosome of the microorganism, various methods known in the art can be used. For example, the initiation codon sequences of endogenous lysC, tkt and pyc genes in the microorganism can be substituted on the chromosome. Alternatively, the corresponding genes having substituted initiation codon sequences can be introduced into the microorganism in the form of a plasmid.

The microorganism may be any strain, as long as it has L-lysine productivity. Specifically it may be a microorganisms of *Corynebacterium* sp. or *Brevibacterium* sp. Examples of the microorganisms of *Corynebacterium* sp. or *Brevibacterium* sp. include *Corynebacterium glutamicum* ATCC13032, *Corynebacterium thermoaminogenes* FERM BP-1539, *Brevibacterium flavum* ATCC 14067, *Brevibacterium lactofermentum* ATCC 13869. Further, L-lysine-producing variants or stains derived therefrom, for example, *Corynebacterium glutamicum* KCCM11016P (this microorganism was disclosed as KFCC10881, and re-deposited to an International Depositary Authority under the Budapest Treaty with Accession No. KCCM11016P, Korean Patent No. 10-0159812, Korean Patent No. 10-0397322) and *Corynebacterium glutamicum* KFCC 11001, may be included. Further more may be *Corynebacterium glutamicum* with Accession No. KCCM11016P.

Specifically, *Corynebacterium glutamicum* with Accession No. KCCM11016P was transformed with a vector comprising the polynucleotide encoding aspartate kinase, transketolase or pyruvate carboxylase wherein the initiation codon is substituted with ATG, to obtain recombinant *Corynebacterium glutamicum*. More Specifically, pDZ-lysC (ATG), pDZ-tkt(ATG) or pDZ-pyc(ATG) vector was introduced into *Corynebacterium glutamicum* with Accession No. KCCM11016P, respectively so as to obtain each recombinant *Corynebacterium glutamicum*.

Further, the microorganism can be transformed with a vector comprising two or more polynucleotides of the polynucleotides encoding aspartate kinase, transketolase or pyruvate carboxylase and having the substituted initiation codon as ATG. Specifically, the pDZ-tkt(ATG) vector comprising the gene of which the initiation codon has been substituted with ATG and encodes transketolase is transformed into *Corynebacterium glutamicum* KCCM11016P-lysC, in which GTG initiation codon of lysC is substituted with ATG, and through second crossover, the initiation codons of lysC and tkt on the chromosome are substituted with ATG so as to obtain *Corynebacterium glutamicum* KCCM11016P-lysC-tkt. Further, the pDZ-pyc(ATG) vector comprising the polynucleotide of which the initiation codon has been substituted with ATG and encodes pyruvate carboxylase is transformed into KCCM11016P-lysC, in which GTG initiation codon of lysC is substituted with ATG, and through second crossover, the initiation codons of lysC and pyc on the chromosome are substituted with ATG so as to obtain KCCM11016P-lysC-pyc. Furthermore, the pDZ-tkt(ATG) vector is transformed into KCCM11016P-lysC-pyc as prepared above, in which GTG initiation codon of lysC and pyc is substituted with ATG, and through second crossover, the initiation codons of lysC, pyc and tkt on the chromosome are substituted with ATG so as to obtain KCCM11016P-lysC-pyc-tkt. It was confirmed that the initiation codons of lysC, pyc and tkt can be also substituted with ATG in another lysine-producing strains belonging to *Corynebacterium glutamicum*, KFCC10750 (this microorganism was disclosed as KFCC10750, and re-deposited to an International Depositary Authority under the Budapest Treaty with Accession No. KCCM11347P, Korean Patent No. 10-0073610), KCCM10770P (Korean Patent No. 10-0924065), CJ3P (Genome Biology 2012, 13:R40) in the same manner. These results suggest that the modified polynucleotides of the present invention can be stably introduced into various strains belonging to *Corynebacterium* sp., thereby increasing L-lysine productivity.

Specifically, the transformant KCCM11016P-lysC-pyc-tkt, which was obtained by introducing pDZ-lysC(ATG), pDZ-tkt(ATG) and pDZ-pyc(ATG) vectors including the polynucleotides encoding aspartate kinase, transketolase and pyruvate carboxylase into *Corynebacterium glutamicum* KCCM11016P, was designated as *Corynebacterium glutamicum* CA01-2059, and deposited on May 2, 2011 at the Korean Culture Center of Microorganisms (hereinafter, abbreviated to "KCCM"), which is an International Depositary Authority under the Budapest Treaty, under Accession No. KCCM11188P. It is deposited by an International Depositary Authority under the Budapest Treaty.

The microorganism according to the present invention is characterized in that the initiation codons of the wild-type genes encoding the above enzymes are substituted with ATG, and therefore, the microorganism has enhanced activities of aspartate kinase, transketolase and pyruvate carboxylase compared to endogenous activities thereof, resulting from remarkable improvement in translation levels of mRNAs transcribed from the lysC, tkt and pyc genes into the proteins.

As used herein, the term "endogenous activity" means the activity of an enzyme in a native microorganism, and for example, the activity of aspartate kinase, transketolase or pyruvate carboxylase in a native microorganism belonging to *Corynebacterium* sp. The term "enhanced endogenous activity" means that the activity is further improved compared to that of the native enzyme.

Specifically, when the aspartate kinase activity of the strain in which the initiation codon of lysC gene was substituted with ATG was compared to that of the parent strain KCCM11016P, 2.73-fold increase in the aspartate kinase activity was observed (Table 4). Further, when the transketolase activity of the strain in which the initiation codon of tkt gene was substituted with ATG was compared to that of the parent strain KCCM11016P, 3.5-fold increase in the transketolase activity was observed (Table 5). Furthermore, when the pyruvate carboxylase activity of the strain in which the initiation codon of pyc gene is substituted with ATG was compared to that of the parent strain KCCM11016P, 1.89-fold increase in the pyruvate carboxylase activity was observed (Table 6).

It was found that L-lysine productivity of the microorganism can be increased by improving the activity of aspartate kinase, transketolase, pyruvate carboxylase or a combination thereof.

In the present invention, the amounts of L-lysine produced in the L-lysine-producing strains, *Corynebacterium glutamicum* KCCM11016P-lysC, KCCM11016P-tkt, KCCM11016P-pyc, KCCM11016P-lysC-tkt, KCCM11016P-lysC-pyc, and KCCM11016P-lysC-pyc-tkt were measured, and as a result, they showed a remarkable improvement in the L-lysine production compared to the parent strain KCCM11016P (Table 7). Also, another lysine-producing strains belonging to *Corynebacterium glutamicum*, KFCC10750 (Korean Patent No. 10-0073610), KCCM10770P (Korean Patent No. 10-0924065), and CJ3P (Genome Biology 2012, 13:R40), in which initiation codons of lysC, pyc and tkt were substituted with ATG, showed a remarkable improvement in the L-lysine production compared to the parent strain (Tables 8~10). These results suggest that microorganisms having one type of modified polynucleotides encoding LysC, Tkt, or Pyc, or having two types of the modified polynucleotides encoding the enzymes, or having three types of modified polynucleotides encoding the enzymes and having the substituted initiation codon as ATG on the chromosome, also showed remarkably improved L-lysine productivity compared to the wild-type microorganism having GTG or TTG initiation codon.

In still another aspect, the present invention provides a method for producing L-lysine, comprising the steps of culturing the microorganism as described above; and recovering L-lysine from the cultured microorganism or the culture broth.

For the cultivation, various methods of producing L-lysine using a microorganism which are widely known in the art can be used. The cultivation can be carried out according to the widely known method, and conditions for the cultivation, including temperature, time, pH of medium, etc. may be controlled properly. A detailed description of the cultivation is given in the following document [Chmiel; Bioprozesstechnik 1. Einfuhrung in die Bioverfahrenstechnik (Gustav Fischer Verlag, Stuttgart, 1991), and Storhas; Bioreaktoren and periphere Einrichtungen (Vieweg Verlag, Braunschweig/Wiesbaden, 1994)]. Further, the cultivation may include batch culture, continuous culture, and fed-batch culture. Specifically, a batch, fed batch or repeated fed batch process may be operated in a continuous manner, but the present invention is not limited thereto.

For use in the cultivation, a medium must satisfy the requirement of a particular strain employed. Culture media for microorganisms belonging to *Corynebacterium* sp. are well known (e.g., Manual of Methods for General Bacteriology. American Society for Bacteriology. Washington D.C., USA, 1981). Carbon sources to be used may include saccharides and carbohydrates such as glucose, sucrose, lactose, fructose, maltose, starch and cellulose; oils and lipids such as soybean oil, sunflower seed oil, castor oil and coconut oil; fatty acids such as palmitic acid, stearic acid, linoleic acid; alcohols such as glycerol and ethanol; and organic acids such as acetic acid. These materials may be used separately or in combination. Nitrogen sources to be used may include peptone, yeast extract, meat broth, malt extract, corn steep liquor, soybean meal and urea, or inorganic compounds such as ammonium sulfate, ammonium chloride, ammonium phosphate, ammonium carbonate and ammonium nitrate. These nitrogen sources may be used separately or in combination. Phosphorus sources to be used may include dipotassium hydrogen phosphate, potassium dihydrogen phosphate, and corresponding sodium salts. In addition, culture media may contain metal salts such as magnesium sulfate or iron sulfate essential for the growth. Lastly, essential nutrients such as amino acids and vitamins may be used in addition to the above substances. In addition, proper precursors may be added into the culture media. These materials may be properly added into the culture during cultivations in a batch or continuous mode.

The pH of the culture media may be adjusted with a basic compound such as sodium hydroxide, potassium hydroxide or ammonia, or an acidic compound such as phosphoric acid or sulfuric acid. The generation of foam may be restrained using an anti-foaming agent such as fatty acid polyglycol ester. The culture media may be kept under aerobic conditions by introducing oxygen or an oxygen-containing gas (e.g., air) thereto. The culture temperature is typically between 20 and 45° C. and specifically between 25 and 40° C. The culturing is continued until a maximal amount of L-lysine is produced. In this regard, it may be accomplished within 10 to 160 hrs. After being produced, L-lysine may be exported into the culture media or may remain within the cells.

Further, the method for producing L-lysine of the present invention comprises the step of recovering L-lysine from the cultured microorganism or the culture broth. The method of recovering L-lysine from the microorganism or the culture broth is widely known in the art. Examples of the L-lysine recovering method may include filtration, anion exchange chromatography, crystallization and HPLC, but are not limited thereto.

EXAMPLES

Hereinafter, the present invention will be described in more detail with reference to Examples. However, these Examples are for illustrative purposes only, and the invention is not intended to be limited by these Examples.

In the Examples, recombinant vectors for substituting ATG for GTG or TTG initiation codon of lysC gene encoding aspartate kinase, tkt gene encoding transketolase, and pyc gene encoding pyruvate carboxylase derived from the lysine-producing strain, Corynebacterium glutamicum KCCM11016P, were constructed. The vector was transformed into Corynebacterium glutamicum KCCM11016P strain to obtain a strain having the substituted initiation codon on the chromosome, thereby preparing a strain having improved lysine productivity.

Corynebacterium glutamicum KCCM11016P strain used in the present invention is a strain which is resistant to S-(2-aminoethyl) cysteine (hereinafter, referred to as AEC) and is homoserine-leaky, prepared by artificial mutation using wild-type Corynebacterium glutamicum (ATCC 13032) as a parent strain (disclosed as KFCC10881. See Korean Patent No. 10-0159812 and Korean Patent No. 10-0397322). Further, KFCC10750 strain is a Corynebacterium glutamicum L-lysine-producing strain which is homoserine auxotroph and resistant to an L-leucine analog, 4-azaleucine and an antibiotic rifampicin, prepared by artificial mutation (Korean Patent No. 10-0073610), KCCM10770P strain is an L-lysine-producing strain derived from KCCM11016P, which retains two copies of 6 types of the genes constituting the lysine biosynthesis pathway on the chromosome (Korean Patent No. 10-0924065), and CJ3P strain is a Corynebacterium glutamicum strain which has L-lysine productivity by introducing each of P458S, V59A, and T311I mutations into three types of pyc, hom, and lysC genes of the wild type, based on the description by Binder et al. (Genome Biology 2012, 13:R40).

Example 1

Construction of Recombinant Vector (pDZ-lysC(ATG)) Having Substituted ATG Initiation Codon in lysC Derived from Corynebacterium glutamicum and Preparation of Strain Having Substituted Initiation Codon pDZ (see Korean Patent No. 10-0924065) was used as a basic vector for the recombinant vector, which was constructed as follows.

(1) Construction of pDZ-lysC(ATG) Recombinant Vector

In order to acquire lysC gene derived from Corynebacterium glutamicum, chromosomal DNA of a lysine-producing strain (Corynebacterium glutamicum KCCM11016P) prepared by artificial mutation was used as a template. Based on the genbank at the U.S. National Institutes of Health (NIH GenBank), a nucleotide sequence (SEQ ID NO. 13) containing the initiation codon region of lysC gene (NCBI Accession No. NC_003450, Ncg10247) was acquired, and based on this sequence, two pairs of primers (Table 1, SEQ ID NOs. 1~4) for substituting the initiation codon GTG with ATG were synthesized.

PCR was carried out using chromosomal DNA of KCCM11016P as a template and primers of the following Table 1. PfuUltra™ High-Fidelity DNA polymerase (Stratagene) was used as a polymerase, and PCR was performed with 30 cycles of denaturation at 96° C. for 30 seconds; annealing at 55° C. for 30 seconds; and polymerization at 72° C. for 30 seconds. Two DNA fragments thus obtained were cloned into pDZ vector treated with restriction enzyme XbaI using an In-Fusion PCR cloning kit (Clontech), and finally, a pDZ-lysC(ATG) recombinant vector was constructed.

(2) Preparation of Strain

The pDZ-lysC(ATG) vector thus constructed was transformed into KCCM11016P by an electric pulse method (by use of the transformation method according to Appl. Microbiol. Biotechnol. (1999) 52:541-545), and then strains, in which the gene was inserted into the chromosome by homologous recombination, were selected on a selection medium containing 25 mg/L of kanamycin. The successful chromosomal insertion of the vector was confirmed by the blue color of the colonies on a solid medium containing X-gal (5-bromo-4-chloro-3-indolyl-(β-D-galactoside). The strain with the first chromosomal insertion was shaking-cultured (30° C., 8 hours) in a nutrient medium. Then, the cultured strain was serially diluted from $10^{-4}$ to $10^{-10}$, and the diluted culture was plated on a solid medium containing X-gal. Most colonies exhibited blue color, whereas white colonies also existed at a low level. By selecting the white colonies, strains in which the nucleotide sequence at the initiation codon region of lysC was substituted via a second crossover were selected. The nucleotide substitution of the initiation codon in the selected strain was finally confirmed by PCR using the primers of SEQ ID NOs. 1 and 4 and then by analyzing the nucleotide sequence of the target site.

TABLE 1

| Primer | Nucleotide sequence | SEQ ID NO. |
|---|---|---|
| lysC/ATG/FX | CCGGGGATCCTCTAGAct tagggagccatcttttgg | 1 |

TABLE 1-continued

| Primer | Nucleotide sequence | SEQ ID NO. |
|---|---|---|
| lysC/ATG/R | CCAGGGCCATCTTTGTGC | 2 |
| lysC/ATG/F | GCACAAAGATGGCCCTGG | 3 |
| lysC/ATG/RX | GCAGGTCGAC<u>TCTAGA</u>AAG<br>TGACATCAACAATGCGTG | 4 |

Example 2

Construction of Recombinant Vector (pDZ-tkt(ATG)) Having Substituted ATG Initiation Codon in Tkt Derived from *Corynebacterium glutamicum* and Preparation of Strain Having Substituted Initiation Codon There are two codons which are expected as an initiation codon on the sequence of tkt gene. Based on the distance from RBS (Ribosomal binding site) and proteomics, the downstream codon was determined as the initiation codon in the present invention.

(1) Construction of pDZ-Tkt(ATG) Recombinant Vector

In order to acquire tkt gene derived from *Corynebacterium glutamicum*, chromosomal DNA of KCCM11016P was used as a template. Based on the genbank at the U.S. National Institutes of Health (NIH GenBank), a nucleotide sequence (SEQ ID NO. 14) containing the initiation codon region of tkt gene (NCBI Accession No. NC_003450, Ncg11512) was acquired, and based on this sequence, two pairs of primers (Table 2, SEQ ID NOs. 5~8) for substituting the initiation codon TTG with ATG were synthesized.

PCR was carried out using chromosomal DNA of KCCM11016P as a template and primers of the following Table 2 under the conditions of Example 1-1. Two DNA fragments thus obtained were cloned into pDZ vector treated with restriction enzyme XbaI using an In-Fusion PCR cloning kit (Clontech), and finally, a pDZ-tkt(ATG) recombinant vector was constructed.

(2) Preparation of Strain

The pDZ-tkt(ATG) vector thus constructed was transformed into the lysine-producing strain KCCM11016P in the same manner as in Example 1-2, and KCCM11016P-tkt, in which the initiation codon of tkt on the chromosome was substituted with ATG via a second crossover, was obtained. The nucleotide substitution of the initiation codon of the gene was finally confirmed by PCR using the primers of SEQ ID NOs. 5 and 8 and then by analyzing the nucleotide sequence of the target site.

TABLE 2

| Primer | Nucleotide sequence | SEQ ID NO. |
|---|---|---|
| tkt/ATG/FX | CCG GGG ATC <u>CTC TAG A</u> GAA<br>ATA GAT GGG TGT AGA CG | 5 |
| tkt/ATG/R4 | GTGACAGCGTCATGGTGGTCAAT | 6 |
| tkt/ATG/F4 | ATTGACCACCATGACGCTGTCAC | 7 |
| tkt/ATG/RX | GCA GGT CGA <u>CTC TAG A</u> CGC<br>AGA GCC TTC AGGTCA TC | 8 |

Example 3

Construction of Recombinant Vector (pDZ-pyc(ATG)) Having Substituted ATG Initiation Codon in Pyc Derived from *Corynebacterium glutamicum* and Preparation of Strain Having Substituted Initiation Codon (1) Construction of pDZ-Pyc(ATG) Recombinant Vector In order to acquire pyc gene derived from *Corynebacterium glutamicum*, chromosomal DNA of KCCM11016P was used as a template. Based on the genbank at the U.S. National Institutes of Health (NIH GenBank), a nucleotide sequence (SEQ ID NO. 15) containing the initiation codon region of pyc gene (NCBI Accession No. NC_003450, Ncg10659) was acquired, and based on this sequence, two pairs of primers (Table 3, SEQ ID NOs. 9~12) for substituting the initiation codon GTG with ATG were synthesized.

PCR was carried out using chromosomal DNA of KCCM11016P as a template and primers of the following Table 3 under the conditions of Example 1-1. Two DNA fragments thus obtained were cloned into pDZ vector treated with restriction enzyme XbaI using an In-Fusion PCR cloning kit (Clontech), and finally, a pDZ-pyc(ATG) recombinant vector was constructed.

(2) Preparation of Strain

The pDZ-pyc(ATG) vector thus constructed was transformed into the lysine-producing strain KCCM11016P in the same manner as in Example 1-2, and KCCM11016P-pyc, in which the initiation codon of pyc on the chromosome was substituted with ATG via a second crossover, was obtained. The nucleotide substitution of the initiation codon of the gene was finally confirmed by PCR using the primers of SEQ ID NOs. 9 and 12 and then by analyzing the nucleotide sequence of the target site.

| Primer | Nucleotide sequence | SEQ ID NO. |
|---|---|---|
| pyc/ATG/FX | CCGGGGATCC<u>TCTAGA</u>TTTTGGGG<br>AAAAGTGCAAAG | 9 |
| pyc/ATG/R | GAGTCGACAtTAGAGTAAT | 10 |
| pyc/ATG/F | ATTACTCTAaTGTCGACTC | 11 |
| pyc/ATG/RX | GCAGGTCGAC<u>TCTAGA</u>GGGCATTT<br>TCAGACAGGAAG | 12 |

Example 4

Measurement of Enzymatic Activity of Aspartate Kinase in Strain Having Substituted ATG Initiation Codon in lysC Gene The cells in the exponential phase were collected by centrifugation (5,000 rpm, 15 minutes) and washed three times with 0.1% Tris.HCl (pH 8.0) buffer, and then suspended in the same buffer for a turbidity at 610 nm of 160. The cells were disrupted for 6 minutes using a bead beater after glass beads added at 1.25 g/1.5 ml of the suspension. The supernatant was collected by centrifugation (15,000 rpm, 20 minutes), and quantitatively measured for protein content by a Bradford method (Bradford, M. M 1976. Anal. Biochem. 72:248-254) and used as a crude protein solution for measuring the enzymatic activity of aspartate kinase (LysC). In order to quantify the enzymatic activity of LysC, about 0.05 mL of the crude protein solution was added to a reaction solution containing 0.1M Tris.HCl (pH 8.0), 0.01M magnesium chloride ($MgCl_2$), 0.6M hydroxylamine.HCl (pH 7.0), 4 mM ATP, and 0.2M aspartate to initiate the reaction. The mixture was allowed to react at 30° C. for 30 minutes, and a stop solution (10% $FeCl_2$, 3.3% TCA, 0.7 N HCl) was added to terminate the reaction. The supernatant was collected by centrifugation, and absorbance at 540 nm was measured. The unit (U) of the LysC enzymatic activity was defined as nmole of the aspartate hydroxamate produced by 1 mg of protein for 1 minute.

KCCM11016P-lysC strain was observed to have 2.73-fold higher LysC activity than that of the parent strain KCCM11016P (Table 4).

TABLE 4

LysC enzymatic activity

| Strain | Enzymatic activity (Fold) LysC |
|---|---|
| KCCM11016P | 1.00 |
| KCCM11016P-lysC | 2.73 |

Example 5

Measurement of Enzymatic Activity of Transketolase in Strain Having Substituted ATG Initiation Codon in tkt Gene The cells in the exponential phase were collected by centrifugation (5,000 rpm, 15 minutes) and washed three times with 0.1% Tris.HCl (pH 7.5) buffer, and then suspended in the same buffer for a turbidity at 610 nm of 160. The cells were disrupted for 6 minutes using a bead beater after glass beads added at 1.25 g/1.5 ml of the suspension. The supernatant was collected by centrifugation (15,000 rpm, 20 minutes), and quantitatively measured for protein content by a Bradford method and used as a crude protein solution for measuring the enzymatic activity of transketolase (Tkt). In order to quantify the enzymatic activity of Tkt, the crude protein solution was added to a reaction solution containing 0.1M Tris.HCl(pH7.5), 10 mM D-R5P, 2 mM D-Xu5P, 10 μM ThDP, 1.2 mM $MgCl_2$, 100 μM NADH, 1 unit triosephosphate isomerase, unit glycerol-3-phosphate dehydrogenase per 1 ml to initiate the reaction. The mixture was allowed to react at 30° C. for 20~30 minutes, and absorbance at 340 nm was measured. The unit (U) of the Tkt enzymatic activity was defined as the amount (mg) of the enzyme catalyzing production of 1 μmol of glyceraldehyde 3-phosphate for 1 minute, and specific activity was defined as units/mg (Biochem. J. (2004)382, 759-767).

KCCM11016P-tkt strain was observed to have 3.5-fold higher Tkt activity than that of the parent strain KCCM11016P (Table 5).

TABLE 5

Tkt enzymatic activity

| Strain | Enzymatic activity (Fold) Tkt |
|---|---|
| KCCM11016P | 1.00 |
| KCCM11016P-tkt | 3.5 |

Example 6

Measurement of Enzymatic Activity of Pyruvate Carboxylase in Strain Having Substituted ATG Initiation Codon in pyc Gene The cells in the exponential phase were collected by centrifugation (5,000 rpm, 15 minutes) and washed twice with mM Tris.HCl (pH 6.3) buffer containing 50 mM sodium chloride (NaCl), and then suspended in 100 mM HEPES (pH 7.5) buffer containing 20% glycerol. CTAB was added to the suspension to a concentration of 0.3%, and left on ice for 1 minute. The cells were collected by centrifugation (5,000 rpm, 10 minutes) and then suspended in 100 mM Tris.HCl (pH 7.3) buffer. The protein content was quantitatively measured by a Bradford method and used as a crude protein solution for measuring the enzymatic activity of pyruvate carboxylase (Pyc). In order to quantify the enzymatic activity of Pyc, the crude protein solution was added to a reaction solution containing 25 mM $NaHCO_3$, 5 mM $MgCl_2$, 3 mM pyruvate, and 4 mM ATP to initiate the reaction. The mixture was allowed to react at 30° C. for 1.5 minutes, and 80 μl of a stop solution (30% o-phosphoric acid) was added to terminate the reaction. The supernatant was collected by centrifugation (12,000 rpm, 15 min, 4° C.). 50 μl of the supernatant, 150 mM Tris.HCl (pH 7.8), 150 μM NADH, and 2.5 U lactate dehydrogenase were added per 1 ml and absorbance at 340 nm was measured at 37° C. The unit (U) of the Pyc enzymatic activity was defined as nmole of the lactate produced by 1 mg of protein for 1 minute.

KCCM11016P-pyc strain was observed to have 1.89-fold higher Pyc activity than that of the parent strain KCCM11016P (Table 6).

TABLE 6

Pyc enzymatic activity

| Strain | Enzymatic activity (Fold) Pyc |
|---|---|
| KCCM11016P | 1.00 |
| KCCM11016P-pyc | 1.89 |

Example 7

Development of KCCM11016P-Derived Strains Having Substituted ATG Initiation Codons in Two or More Genes of lysC, tkt, and pyc Genes As the recombinant vectors, pDZ-lysC(ATG) pDZ-tkt (ATG) pDZ-pyc(ATG) prepared in Examples 1, 2, and 3 were used, and the preparation process is as follows.

The pDZ-tkt(ATG) vector was transformed into KCCM11016P-lysC of Example 1, in which GTG initiation codon of lysC was substituted with ATG, and through second crossover, the initiation codons of lysC and tkt on the chromosome were substituted with ATG so as to obtain KCCM11016P-lysC-tkt. The nucleotide substitution of the initiation codon of the gene was finally confirmed by PCR using the primers of SEQ ID NOs. 5 and 8 and then by analyzing the nucleotide sequence of the target site.

In the same manner as in Example 1, the pDZ-pyc(ATG) vector was transformed into KCCM11016P-lysC of Example 1, in which GTG initiation codon of lysC was substituted with ATG, and through second crossover, the initiation codons of lysC and pyc on the chromosome were substituted with ATG so as to obtain KCCM11016P lysC-pyc. The nucleotide substitution of the initiation codon of the gene was finally confirmed by PCR using the primers of SEQ ID NOs. 9 and 12 and then by analyzing the nucleotide sequence of the target site.

The pDZ-tkt(ATG) vector was transformed into KCCM11016P-lysC-pyc of the present Example, in which GTG initiation codon of lysC and pyc was substituted with ATG, and through second crossover, the initiation codons of lysC, pyc and tkt on the chromosome were substituted with ATG so as to obtain KCCM11016P-lysC-pyc-tkt. The nucleotide substitution of the initiation codon of the gene was finally confirmed by PCR using the primers of SEQ ID NOs. 5 and 8 and then by analyzing the nucleotide sequence of the target site.

The above combinations of the genes are for illustrative purposes only, and the scope of the gene combinations is not intended to be limited thereto.

Example 8

Production of Lysine in Strain Having Substituted ATG Initiation Codon

KCCM11016P-lysC, KCCM11016P-tkt, KCCM11016P-pyc, KCCM11016P-lysC-tkt, KCCM11016P-lysC-pyc, KCCM11016P-lysC-pyc-tkt finally prepared in Examples 1, 2, 3, and 7 were cultured for L-lysine production by the following method.

The parent strain KCCM11016P and KCCM11016P-lysC, KCCM11016P-tkt, KCCM11016P-pyc, KCCM11016P-lysC-tkt, KCCM11016P-lysC-pyc, KCCM11016P-lysC-pyc-tkt were inoculated in respective 250 ml corner-baffled flasks containing 25 ml of the seed medium described below, and the resultant was cultured at 30° C. with shaking at 200 rpm for 20 hours. 1 mL of the resulting seed culture broth was inoculated into a 250 ml corner-baffled flask containing 24 ml of the production medium described below, and cultured at 30° C. with shaking (200 rpm) for 120 hours.

After completing the culture, the quantity of produced L-lysine was measured by HPLC. The results of measuring L-lysine in the culture broths of KCCM11016P and KCCM11016P-lysC, KCCM11016P-tkt, KCCM11016P-pyc, KCCM11016P-lysC-tkt, KCCM11016P-lysC-pyc, KCCM11016P-lysC-pyc-tkt are shown in the following Table 7.

TABLE 7

| | Lysine (g/l) | | |
|---|---|---|---|
| Strain | Batch 1 | Batch 2 | Batch 3 |
| KCCM11016P | 45.2 | 44.7 | 45.6 |
| KCCM11016P-lysC | 47.5 | 46.2 | 47.9 |
| KCCM11016P-tkt | 47.4 | 48.5 | 47.0 |
| KCCM11016P-pyc | 47.9 | 46.3 | 47.8 |
| KCCM11016P-lysC-tkt | 49.7 | 49.3 | 49.2 |
| KCCM11016P-lysC-pyc | 50.1 | 48.9 | 49.6 |
| KCCM11016P-lysC-pyc-tkt | 50.7 | 50.2 | 51.1 |

Seed Medium (pH 7.0)

20 g of raw sugar, 10 g of peptone, 5 g of yeast extract, 1.5 g of urea, 4 g of $KH_2PO_4$, 8 g of $K_2HPO_4$, 0.5 g of $MgSO_4$ $7H_2O$, 100 µg of biotin, 1000 µg of Thiamine-HCl, 2000 µg of calcium-pantothenate, 2000 µg of nicotine amide (in 1 liter of distilled water)

Production Medium (pH 7.0)

100 g of glucose, 40 g of $(NH_4)_2SO_4$, 2.5 g of soybean protein, 5 g of corn steep solids, 3 g of urea, 1 g of $KH_2PO_4$, 0.5 g of $MgSO_4$ $7H_2O$, 100 µg of biotin, 1000 µg of Thiamine-HCl, 2000 µg of calcium-pantothenate, 3000 µg of nicotine amide, 30 g of $CaCO_3$ (in 1 liter of distilled water)

As shown in Table 7, Corynebacterium glutamicum KCCM11016P-lysC, KCCM11016P-tkt, KCCM11016P-pyc, KCCM11016P-lysC-tkt, and KCCM11016P-lysC-pyc having substituted ATG initiation codon were found to show 4-9% increase in L-lysine productivity, compared with the parent strain KCCM11016P. In particular, KCCM11016P-lysC-pyc-tkt introduced with all three genes was found to show an increase in L-lysine productivity as high as 12%, compared to the parent strain KCCM11016P.

Example 9

Development of KFCC10750-Derived Strain Having Substituted ATG Initiation Codons in lysC, tkt, and pyc Genes and Comparison of Lysine Productivity In order to examine whether substitution of the initiation codons with ATG in lysC, pyc, and tkt genes also affects lysine productivity in other lysine-producing strains belonging to Corynebacterium glutamicum, the L-lysine-producing strain Corynebacterium glutamicum KFCC10750 (Korean Patent No. 10-0073610) was introduced with all three genes which showed the most excellent effect of increasing lysine productivity in Example 8 so as to prepare a recombinant strain, which was named as KFCC10750-lysC-pyc-tkt. The strain was cultured in the same manner as in Example 8, and the L-lysine concentration was analyzed (Table 8).

TABLE 8

| | Lysine (g/l) | | |
|---|---|---|---|
| Strain | Batch 1 | Batch 2 | Batch 3 |
| KFCC10750 | 38.3 | 38 | 38.5 |
| KFCC10750-lysC-pyc-tkt | 44.1 | 43.8 | 44.5 |

As shown in Table 8, Corynebacterium glutamicum KFCC10750-lysC-pyc-tkt introduced with all three genes showed 15% increase in the lysine productivity, compared to the parent strain KFCC10750.

Example 10

Development of KCCM10770P-Derived Strain Having Substituted ATG Initiation Codons in lysC, Tkt, Pyc Genes and Comparison of Lysine Productivity Another L-lysine-producing strain Corynebacterium glutamicum KCCM10770P (Korean Patent No. 10-0924065) was introduced with all three genes which showed the most excellent effect of increasing lysine productivity in Example 8 so as to prepare a recombinant strain, which was named as KCCM10770P-lysC-pyc-tkt. The strain was cultured in the same manner as in Example 8, and the L-lysine concentration was analyzed (Table 9).

TABLE 9

| Strain | Lysine (g/l) | | |
|---|---|---|---|
| | Batch 1 | Batch 2 | Batch 3 |
| KCCM10770P | 47.8 | 47.2 | 47.5 |
| KCCM10770P-lysC-pyc-tkt | 52.8 | 52.8 | 52.4 |

As shown in Table 9, *Corynebacterium glutamicum* KCCM10770P-lysC-pyc-tkt introduced with all three genes showed 11% increase in the lysine productivity, compared to the parent strain KCCM10770P.

Example 11

Development of CJ3P-Derived Strain Having Substituted ATG Initiation Codons in lysC, tkt, pyc Genes and Comparison of Lysine Productivity Still another L-lysine-producing strain *Corynebacterium glutamicum* CJ3P (Binder et al. Genome Biology 2012, 13:R40) was introduced with all three genes which showed the most excellent effect of increasing lysine productivity in Example 8 so as to prepare a recombinant strain, which was named as CJ3P-lysC-pyc-tkt. The strain was cultured in the same manner as in Example 8, and the L-lysine concentration was analyzed (Table 10).

TABLE 10

| Strain | Lysine (g/l) | | |
|---|---|---|---|
| | Batch 1 | Batch 2 | Batch 3 |
| CJ3P | 8.3 | 8 | 8.4 |
| CJ3P-lysC-pyc-tkt | 9.7 | 9.6 | 10.0 |

As shown in Table 10, *Corynebacterium glutamicum* CJ3P-lysC-pyc-tkt introduced with all three genes showed 18% increase in the lysine productivity, compared to the parent strain CJ3P.

EFFECT OF THE INVENTION

The present invention provides a *Corynebacterium* sp. microorganism having improved L-lysine productivity, in which initiation codons of one or more genes encoding aspartate kinase, transketolase, or pyruvate carboxylase are substituted to enhance activities of the corresponding enzymes, compared to their endogenous activities in a native microorganism.

---

What is claimed is:

1. A lysine-producing microorganism that has enhanced activities of two or more enzymes selected from the group consisting of aspartate kinase, transketolase and pyruvate carboxylase compared to endogenous activities thereof,
   wherein the initiation codons of polynucleotides encoding the enzymes are substituted with ATG,
   wherein the polynucleotides whose initiation codon are substituted with ATG are selected from the group consisting of polynucleotides that comprise the nucleotide sequences of SEQ ID NOS:16, 17 and 18, and
   wherein the microorganism produces more lysine than an unmodified microorganism.

2. The microorganism according to claim 1, wherein the microorganism is *Corynebacterium glutamicum*.

3. A method for producing L-lysine, comprising the steps of culturing the microorganism of claim 1 or claim 2; and recovering L-lysine from the cultured microorganism or the culture broth.

4. The lysine-producing microorganism according to claim 1, wherein the initiation codon of the polynucleotide encoding aspartate kinase (LysC) or pyruvate carboxylase (Pyc) prior to the modification is GTG and the initiation codon of the polynucleotide encoding transketolase (Tkt) prior to the modification is TTG.

* * * * *

UNITED STATES PATENT AND TRADEMARK OFFICE
CERTIFICATE OF CORRECTION

PATENT NO. : 9,593,354 B2  Page 1 of 1
APPLICATION NO. : 14/367818
DATED : March 14, 2017
INVENTOR(S) : Kwang Ho Lee et al.

It is certified that error appears in the above-identified patent and that said Letters Patent is hereby corrected as shown below:

On the Title Page

Item (56):
"KR 102008025355 A 3/2008" should read, --KR 1020080025355 A 3/2008--.

Signed and Sealed this
Twenty-fifth Day of April, 2017

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 36
<212> TYPE: DNA
<213> ORGANISM: Artificial Sequence
<220> FEATURE:
<223> OTHER INFORMATION: primer lysC/ATG/FX

<400> SEQUENCE: 1
ccggggatcc tctagactta gggagccatc ttttgg                                36

<210> SEQ ID NO 2
<211> LENGTH: 18
<212> TYPE: DNA
<213> ORGANISM: Artificial Sequence
<220> FEATURE:
<223> OTHER INFORMATION: primer lysC/ATG/R

<400> SEQUENCE: 2
ccagggccat ctttgtgc                                                    18

<210> SEQ ID NO 3
<211> LENGTH: 18
<212> TYPE: DNA
<213> ORGANISM: Artificial Sequence
<220> FEATURE:
<223> OTHER INFORMATION: primer lysC/ATG/F

<400> SEQUENCE: 3
gcacaaagat ggccctgg                                                    18

<210> SEQ ID NO 4
<211> LENGTH: 36
<212> TYPE: DNA
<213> ORGANISM: Artificial Sequence
<220> FEATURE:
<223> OTHER INFORMATION: primer lysC/ATG/RX

<400> SEQUENCE: 4
```

```
gcaggtcgac tctagaagtg acatcaacaa tgcgtg                                    36
```

<210> SEQ ID NO 5
<211> LENGTH: 36
<212> TYPE: DNA
<213> ORGANISM: Artificial Sequence
<220> FEATURE:
<223> OTHER INFORMATION: primer tkt/ATG/FX

<400> SEQUENCE: 5

```
ccggggatcc tctagagaaa tagatgggtg tagacg                                    36
```

<210> SEQ ID NO 6
<211> LENGTH: 23
<212> TYPE: DNA
<213> ORGANISM: Artificial Sequence
<220> FEATURE:
<223> OTHER INFORMATION: primer tkt/ATG/R4

<400> SEQUENCE: 6

```
gtgacagcgt catggtggtc aat                                                  23
```

<210> SEQ ID NO 7
<211> LENGTH: 23
<212> TYPE: DNA
<213> ORGANISM: Artificial Sequence
<220> FEATURE:
<223> OTHER INFORMATION: primer tkt/ATG/F4

<400> SEQUENCE: 7

```
attgaccacc atgacgctgt cac                                                  23
```

<210> SEQ ID NO 8
<211> LENGTH: 36
<212> TYPE: DNA
<213> ORGANISM: Artificial Sequence
<220> FEATURE:
<223> OTHER INFORMATION: primer tkt/ATG/RX

<400> SEQUENCE: 8

```
gcaggtcgac tctagacgca gagccttcag gtcatc                                    36
```

<210> SEQ ID NO 9
<211> LENGTH: 36
<212> TYPE: DNA
<213> ORGANISM: Artificial Sequence
<220> FEATURE:
<223> OTHER INFORMATION: primer pyc/ATG/FX

<400> SEQUENCE: 9

```
ccggggatcc tctagatttt ggggaaaagt gcaaag                                    36
```

<210> SEQ ID NO 10
<211> LENGTH: 19
<212> TYPE: DNA
<213> ORGANISM: Artificial Sequence
<220> FEATURE:
<223> OTHER INFORMATION: primer pyc/ATG/R

<400> SEQUENCE: 10

```
gagtcgacat tagagtaat                                                       19
```

<210> SEQ ID NO 11
<211> LENGTH: 19
<212> TYPE: DNA

```
<213> ORGANISM: Artificial Sequence
<220> FEATURE:
<223> OTHER INFORMATION: primer pyc/ATG/F

<400> SEQUENCE: 11
attactctaa tgtcgactc                                            19

<210> SEQ ID NO 12
<211> LENGTH: 36
<212> TYPE: DNA
<213> ORGANISM: Artificial Sequence
<220> FEATURE:
<223> OTHER INFORMATION: primer pyc/ATG/RX

<400> SEQUENCE: 12
gcaggtcgac tctagagggc attttcagac aggaag                         36

<210> SEQ ID NO 13
<211> LENGTH: 1266
<212> TYPE: DNA
<213> ORGANISM: Corynebacterium glutamicum lysC

<400> SEQUENCE: 13
gtggccctgg tcgtacagaa atatggcggt tcctcgcttg agagtgcgga acgcattaga     60
aacgtcgctg aacggatcgt tgccaccaag aaggctggaa atgatgtcgt ggttgtctgc    120
tccgcaatgg gagacaccac ggatgaactt ctagaacttg cagcggcagt gaatcccgtt    180
ccgccagctc gtgaaatgga tatgctcctg actgctggtg agcgtatttc taacgctctc    240
gtcgccatgc tattgagtc ccttggcgca gaagcccaat ctttcacggg ctctcaggct    300
ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg ctttgaacgc tgatgtgtgt gagatttact cggacgttga cggtgtgtat    540
accgctgacc cgcgcatcgt tcctaatgca cagaagctgg aaaagctcag cttcgaagaa    600
atgctggaac ttgctgctgt tggctccaag atttttggtgc tgcgcagtgt tgaatacgct    660
cgtgcattca atgtgccact tcgcgtacgc tcgtcttata gtaatgatcc cggcactttg    720
attgccggct ctatggagga tattcctgtg aagaagcag tccttaccgg tgtcgcaacc    780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc accttcacct gccctcgttc cgacggccgc    960
cgcgcgatgg agatcttgaa gaagcttcag gttcagggca actggaccaa tgtgctttac   1020
gacgaccagg tcggcaaagt ctccctcgtg ggtgctggca tgaagtctca cccaggtgtt   1080
accgcagagt tcatggaagc tctgcgcgat gtcaacgtga acatcgaatt gatttccacc   1140
tctgagattc gtatttccgt gctgatccgt gaagatgatc tggatgctgc tgcacgtgca   1200
ttgcatgagc agttccagct gggcggcgaa gacgaagccg tcgtttatgc aggcaccgga   1260
cgctaa                                                             1266

<210> SEQ ID NO 14
<211> LENGTH: 2094
<212> TYPE: DNA
<213> ORGANISM: Corynebacterium glutamicum tkt

<400> SEQUENCE: 14
```

```
ttgacgctgt caccctgaact tcaggcgctc actgtacgca attacccctc tgattggtcc      60
gatgtggaca ccaaggctgt agacactgtt cgtgtcctcg ctgcagacgc tgtagaaaac     120
tgtggctccg gccacccagg caccgcaatg agcctggctc cccttgcata caccttgtac     180
cagcgggtta tgaacgtaga tccacaggac accaactggg caggccgtga ccgcttcgtt     240
ctttcttgtg gccactcctc tttgacccag tacatccagc tttacttggg tggattcggc     300
cttgagatgg atgacctgaa ggctctgcgc acctgggatt ccttgacccc aggacaccct     360
gagtaccgcc acaccaaggg cgttgagatc accactggcc tcttggcca gggtcttgca      420 tctgcagttg gtatggccat ggctgctcgt cgtgagcgtg gcctattcga cccaaccgct     480
gctgagggcg aatccccatt cgaccaccac atctacgtca ttgcttctga tggtgacctg     540
caggaaggtc tcacctctga ggcatcctcc atcgctggca cccagcagct gggcaacctc     600
atcgtgttct gggatgacaa ccgcatctcc atcgaagaca cactgagat cgctttcaac      660 gaggacgttg ttgctcgtta caaggcttac ggctggcaga ccattgaggt tgaggctggc     720
gaggacgttg cagcaatcga agctgcagtg gctgaggcta agaaggacac caagcgacct     780
accttcatcc gcgttcgcac catcatcggc ttcccagctc caactatgat gaacaccggt     840
gctgtgcacg gtgctgctct tggcgcagct gaggttgcag caaccaagac tgagcttgga     900
ttcgatcctg aggctcactt cgcgatcgac gatgaggtta tcgctcacac ccgctccctc     960
gcagagcgcg ctgcacagaa gaaggctgca tggcaggtca agttcgatga gtgggcagct    1020
gccaaccctg agaacaaggc tctgttcgat cgcctgaact cccgtgagct tccagcgggc    1080
tacgctgacg agctcccaac atgggatgca gatgagaagg gcgtcgcaac tcgtaaggct    1140
tccgaggctg cacttcaggc actgggcaag acccttcctg agctgtgggg cggttccgct    1200
gacctcgcag gttccaacaa caccgtgatc aagggctccc cttccttcgg ccctgagtcc    1260
atctccaccg agacctggtc tgctgagcct tacggccgta acctgcactt cggtatccgt    1320
gagcacgcta tgggatccat cctcaacggc atttccctcc acggtggcac ccgcccatac    1380
ggcggaacct tcctcatctt ctccgactac atgcgtcctg cagttcgtct tgcagctctc    1440
atggagaccg acgcttacta cgtctggacc cacgactcca tcggtctggg cgaagatggc    1500
ccaacccacc agcctgttga aaccttggct gcactgcgcg ccatcccagg tctgtccgtc    1560
ctgcgtcctg cagatgcgaa cgagaccgcc caggcttggg ctgcagcact tgagtacaag    1620
gaaggcccta agggtcttgc actgaccgc cagaacgttc ctgttctgga aggcaccaag    1680
gagaaggctg ctgaaggcgt tcgccgcggt ggctacgtcc tggttgaggg ttccaaggaa    1740
accccagatg tgatcctcat gggctccggc tccgaggttc agcttgcagt taacgctgcg    1800
aaggctctgg aagctgaggg cgttgcagct cgcgttgttt ccgttccttg catggattgg    1860
ttccaggagc aggacgcaga gtacatcgag tccgttctgc ctgcagctgt gaccgctcgt    1920
gtgtctgttg aagctggcat cgcaatgcct tggtaccgct tcttgggcac ccagggccgt    1980
gctgtctccc ttgagcactt cggtgcttct gcggattacc agaccctgtt tgagaagttc    2040
ggcatcacca ccgatgcagt cgtggcagcg gccaaggact ccattaacgg ttaa          2094
```

<210> SEQ ID NO 15
<211> LENGTH: 3423
<212> TYPE: DNA
<213> ORGANISM: Corynebacterium glutamicum pyc

<400> SEQUENCE: 15

```
gtgtcgactc acacatcttc aacgcttcca gcattcaaaa agatcttggt agcaaaccgc      60
ggcgaaatcg cggtccgtgc tttccgtgca gcactcgaaa ccggtgcagc cacggtagct     120 atttacccccc gtgaagatcg gggatcattc caccgctctt ttgcttctga agctgtccgc    180
attggtaccg aaggctcacc agtcaaggcg tacctggaca tcgatgaaat tatcggtgca     240
gctaaaaaag ttaaagcaga tgccatttac ccgggatacg gcttcctgtc tgaaaatgcc    300
cagcttgccc gcgagtgtgc ggaaaacggc attactttta ttggcccaac cccagaggtt    360
cttgatctca ccggtgataa gtctcgcgcg gtaaccgccg cgaagaaggc tggtctgcca    420
gttttggcgg aatccacccc gagcaaaaac atcgatgaga tcgttaaaag cgctgaaggc    480
cagacttacc ccatctttgt gaaggcagtt gccggtggtg gcggacgcgg tatgcgtttt    540
gttgcttcac ctgatgagct tcgcaaatta gcaacagaag catctcgtga agctgaagcg    600
gctttcggcg atggcgcggt atatgtcgaa cgtgctgtga ttaaccctca gcatattgaa    660
gtgcagatcc ttggcgatca cactggagaa gttgtacacc tttatgaacg tgactgctca    720
ctgcagcgtc gtcaccaaaa agttgtcgaa attgcgccag cacagcattt ggatccagaa    780
ctgcgtgatc gcatttgtgc ggatgcagta aagttctgcc gctccattgg ttaccagggc    840
gcgggaaccg tggaattctt ggtcgatgaa aagggcaacc acgtcttcat cgaaatgaac    900
ccacgtatcc aggttgagca caccgtgact gaagaagtca ccgaggtgga cctggtgaag    960
gcgcagatgc gcttggctgc tggtgcaacc ttgaaggaat tgggtctgac ccaagataag   1020
atcaagaccc acggtgcagc actgcagtgc cgcatcacca cggaagatcc aaacaacggc   1080
ttccgcccag ataccggaac tatcaccgcg taccgctcac caggcggagc tggcgttcgt   1140
cttgacggtg cagctcagct cggtggcgaa atcaccgcac actttgactc catgctggtg   1200
aaaatgacct gccgtggttc cgactttgaa actgctgttg ctcgtgcaca gcgcgcgttg   1260
gctgagttca ccgtgtctgg tgttgcaacc aacattggtt tcttgcgtgc gttgctgcgg   1320
gaagaggact tcacttccaa gcgcatcgcc accggattca ttgccgatca cccgcacctc   1380
cttcaggctc cacctgctga tgatgagcag ggacgcatcc tggattactt ggcagatgtc   1440
accgtgaaca gcctcatgg tgtgcgtcca aaggatgttg cagctcctat cgataagctg   1500
cctaacatca aggatctgcc actgccacgc ggttcccgtg accgcctgaa gcagcttggc   1560
ccagccgcgt ttgctcgtga tctccgtgag caggacgcac tggcagttac tgataccacc   1620
ttccgcgatg cacaccagtc tttgcttgcg acccgagtcc gctcattcgc actgaagcct   1680
gcggcagagg ccgtcgcaaa gctgactcct gagcttttgt ccgtggaggc ctggggcggc   1740
gcgacctacg atgtggcgat gcgtttcctc tttgaggatc cgtgggacag gctcgacgag   1800
ctgcgcgagg cgatgccgaa tgtaaacatt cagatgctgc ttcgcggccg caacaccgtg   1860
ggatacaccc cgtacccaga ctccgtctgc cgcgcgtttg ttaaggaagc tgccagctcc   1920
ggcgtggaca tcttccgcat cttcgacgcg cttaacgacg tctcccagat cgtccagca    1980 atcgacgcag tcctggagac caacaccgcg gtagccgagg tggctatggc ttattctggt   2040
gatctctctg atccaaatga aaagctctac accctggatt actacctaaa gatggcagag   2100
gagatcgtca gtctggcgc tcacatcttg gccattaagg atatggctgg tctgcttcgc   2160
ccagctgcgg taaccaagct ggtcaccgca ctgcgccgtg aattcgatct gccagtgcac   2220
gtgcacaccc acgacactgc gggtggccag ctggcaacct actttgctgc agctcaagct   2280
ggtgcagatg ctgttgacgg tgcttccgca ccactgtctg gcaccacctc ccagccatcc   2340
ctgtctgcca ttgttgctgc attcgcgcac acccgtcgcg ataccggttt gagcctcgag   2400
```

```
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgcgg atcgtttcga actcatcgaa    2580
gacaactacg cagccgttaa tgagatgctg ggacgcccaa ccaaggtcac ccatcctcc    2640 aaggttgttg gcgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgatccgcc tgccagatgt gcgcacccca    3060
ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg gaaggtggcg acttgatcgt cgtcgtttcc    3420
taa                                                                 3423

<210> SEQ ID NO 16
<211> LENGTH: 1266
<212> TYPE: DNA
<213> ORGANISM: Artificial Sequence
<220> FEATURE:
<223> OTHER INFORMATION: lysC with substituted start codon

<400> SEQUENCE: 16
atggccctgg tcgtacagaa atatggcggt tcctcgcttg agagtgcgga acgcattaga     60
aacgtcgctg aacggatcgt tgccaccaag aaggctggaa atgatgtcgt ggttgtctgc    120
tccgcaatgg gagacaccac ggatgaactt ctagaacttg cagcggcagt gaatcccgtt    180
ccgccagctc gtgaaatgga tatgctcctg actgctggtg agcgtatttc taacgctctc    240
gtcgccatgg ctattgagtc ccttggcgca gaagcccaat ctttcacggg ctctcaggct    300
ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg cttttaacgc tgatgtgtgt gagatttact cggacgttga cggtgtgtat    540
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcactttg    720
attgccggct ctatggagga tattcctgtg aagaagcag tccttaccgg tgtcgcaacc    780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc accttcacct gccctcgttc cgacggccgc    960
```

| | |
|---|---|
| cgcgcgatgg agatcttgaa gaagcttcag gttcagggca actggaccaa tgtgctttac | 1020 |
| gacgaccagg tcggcaaagt ctccctcgtg ggtgctggca tgaagtctca cccaggtgtt | 1080 |
| accgcagagt tcatggaagc tctgcgcgat gtcaacgtga acatcgaatt gatttccacc | 1140 |
| tctgagattc gtatttccgt gctgatccgt gaagatgatc tggatgctgc tgcacgtgca | 1200 |
| ttgcatgagc agttccagct gggcggcgaa gacgaagccg tcgtttatgc aggcaccgga | 1260 |
| cgctaa | 1266 |

```
<210> SEQ ID NO 17
<211> LENGTH: 2094
<212> TYPE: DNA
<213> ORGANISM: Artificial Sequence
<220> FEATURE:
<223> OTHER INFORMATION: tkt with substituted start codon

<400> SEQUENCE: 17
```

| | |
|---|---|
| atgacgctgt cacctgaact tcaggcgctc actgtacgca attaccctc tgattggtcc | 60 |
| gatgtggaca ccaaggctgt agacactgtt cgtgtcctcg ctgcagacgc tgtagaaaac | 120 |
| tgtggctccg ccacccagg caccgcaatg agcctggctc cccttgcata caccttgtac | 180 |
| cagcgggtta tgaactaga tccacaggac accaactggg caggccgtga ccgcttcgtt | 240 |
| ctttcttgtg gccactcctc tttgacccag tacatccagc tttacttggg tggattcggc | 300 |
| cttgagatgg atgacctgaa ggctctgcgc acctgggatt ccttgacccc aggacaccct | 360 |
| gagtaccgcc acaccaaggg cgttgagatc accactggcc ctcttggcca gggtcttgca | 420 |
| tctgcagttg gtatggccat ggctgctcgt cgtgagcgtg gcctattcga cccaaccgct | 480 |
| gctgagggcg aatccccatt cgaccaccac atctacgtca ttgcttctga tggtgacctg | 540 |
| caggaaggtg tcacctctga ggcatcctcc atcgctggca cccagcagct gggcaacctc | 600 |
| atcgtgttct gggatgacaa ccgcatctcc atcgaagaca cactgagat cgctttcaac | 660 |
| gaggacgttg ttgctcgtta caaggcttac ggctggcaga ccattgaggt tgaggctggc | 720 |
| gaggacgttg cagcaatcga agctgcagtg ctgaggcta agaaggacac caagcgacct | 780 |
| accttcatcc gcgttcgcac catcatcggc ttcccagctc aactatgat gaacaccggt | 840 |
| gctgtgcacg gtgctgctct tggcgcagct gaggttgcag caaccaagac tgagcttgga | 900 |
| ttcgatcctg aggctcactt cgcgatcgac gatgaggtta tcgctcacac ccgctccctc | 960 |
| gcagagcgcg ctgcacagaa gaaggctgca tggcaggtca agttcgatga gtgggcagct | 1020 |
| gccaaccctg agaacaaggc tctgttcgat cgcctgaact cccgtgagct tccagcgggc | 1080 |
| tacgctgacg agctcccaac atgggatgca gatgagaagg gcgtcgcaac tcgtaaggct | 1140 |
| tccgaggctg cacttcaggc actgggcaag acccttcctg agctgtgggg cggttccgct | 1200 |
| gacctcgcag gttccaacaa caccgtgatc aagggctccc cttccttcgg ccctgagtcc | 1260 |
| atctccaccg agacctggtc tgctgagcct acggccgta acctgcactt cggtatccgt | 1320 |
| gagcacgcta tgggatccat cctcaacggc atttccctcc acggtggcac ccgcccatac | 1380 |
| ggcggaacct tcctcatctt ctccgactac atgcgtcctg cagttcgtct tgcagctctc | 1440 |
| atggagaccg acgcttacta cgtctggacc cacgactcca tcgtctgggc gaagatggc | 1500 |
| ccaacccacc agcctgttga aaccttggct gcactgcgcg ccatcccagg tctgtccgtc | 1560 |
| ctgcgtcctg cagatgcgaa cgagaccgcc caggcttggg ctgcagcact tgagtacaag | 1620 |
| gaaggcccta agggtcttgc actgacccgc cagaacgttc tgttctgga aggcaccaag | 1680 |
| gagaaggctg ctgaaggcgt cgccgcggt ggctacgtcc tggttgaggg ttccaaggaa | 1740 |

| | |
|---|---|
| acccagatg tgatcctcat gggctccggc tccgaggttc agcttgcagt taacgctgcg | 1800 |
| aaggctctgg aagctgaggg cgttgcagct cgcgttgttt ccgttccttg catggattgg | 1860 |
| ttccaggagc aggacgcaga gtacatcgag tccgttctgc ctgcagctgt gaccgctcgt | 1920 |
| gtgtctgttg aagctggcat cgcaatgcct tggtaccgct tcttgggcac ccagggccgt | 1980 |
| gctgtctccc ttgagcactt cggtgcttct gcggattacc agaccctgtt tgagaagttc | 2040 |
| ggcatcacca ccgatgcagt cgtggcagcg gccaaggact ccattaacgg ttaa | 2094 |

<210> SEQ ID NO 18
<211> LENGTH: 3423
<212> TYPE: DNA
<213> ORGANISM: Artificial Sequence
<220> FEATURE:
<223> OTHER INFORMATION: pyc with substituted start codon

<400> SEQUENCE: 18

| | |
|---|---|
| atgtcgactc acacatcttc aacgcttcca gcattcaaaa agatcttggt agcaaaccgc | 60 |
| ggcgaaatcg cggtccgtgc tttccgtgca gcactcgaaa ccggtgcagc cacggtagct | 120 |
| atttaccccc gtgaagatcg gggatcattc caccgctctt tgcttctgaa gctgtccgc | 180 |
| attggtaccg aaggctcacc agtcaaggcg tacctggaca tcgatgaaat tatcggtgca | 240 |
| gctaaaaaag ttaaagcaga tgccatttac ccgggatacg gcttcctgtc tgaaaatgcc | 300 |
| cagcttgccc gcgagtgtgc ggaaaacggc attacttta ttggcccaac cccagaggtt | 360 |
| cttgatctca ccggtgataa gtctcgcgcg gtaaccgccg cgaagaaggc tggtctgcca | 420 |
| gttttggcgg aatccacccc gagcaaaaac atcgatgaga tcgttaaaag cgctgaaggc | 480 |
| cagacttacc ccatctttgt gaaggcagtt gccggtggtg gcggacgcgg tatgcgtttt | 540 |
| gttgcttcac ctgatgagct tcgcaaatta gcaacagaag catctcgtga agctgaagcg | 600 |
| gctttcggcg atggcgcggt atatgtcgaa cgtgctgtga ttaaccctca gcatattgaa | 660 |
| gtgcagatcc ttggcgatca cactggagaa gttgtacacc tttatgaacg tgactgctca | 720 |
| ctgcagcgtc gtcaccaaaa agttgtcgaa attgcgccag cacagcattt ggatccagaa | 780 |
| ctgcgtgatc gcatttgtgc ggatgcagta aagttctgcc gctccattgg ttaccagggc | 840 |
| gcgggaaccg tggaattctt ggtcgatgaa aagggcaacc acgtcttcat cgaaatgaac | 900 |
| ccacgtatcc aggttgagca caccgtgact gaagaagtca ccgaggtgga cctggtgaag | 960 |
| gcgcagatgc gcttggctgc tggtgcaacc ttgaaggaat tgggtctgac ccaagataag | 1020 |
| atcaagaccc acggtgcagc actgcagtgc cgcatcacca cggaagatcc aaacaacggc | 1080 |
| ttccgcccag ataccggaac tatcaccgcg taccgctcac caggcggagc tggcgttcgt | 1140 |
| cttgacggtg cagctcagct cggtggcgaa atcaccgcac actttgactc catgctggtg | 1200 |
| aaaatgacct gccgtggttc cgactttgaa actgctgttg ctcgtgcaca gcgcgcgttg | 1260 |
| gctgagttca ccgtgtctgg tgttgcaacc aacattggtt tcttgcgtgc gttgctgcgg | 1320 |
| gaagaggact tcacttccaa gcgcatcgcc accggattca ttgccgatca cccgcacctc | 1380 |
| cttcaggctc cacctgctga tgatgagcag ggacgcatcc tggattactt ggcagatgtc | 1440 |
| accgtgaaca agcctcatgg tgtgcgtcca aaggatgttg cagctccat cgataagctg | 1500 |
| cctaacatca aggatctgcc actgccacgc ggttcccgtg accgcctgaa gcagcttgcc | 1560 |
| ccagccgcgt tgctcgtga tctccgtgag caggacgcac tggcagttac tgataccacc | 1620 |
| ttccgcgatg cacaccagtc tttgcttgcg acccgagtcc gctcattcgc actgaagcct | 1680 |

```
gcggcagagg ccgtcgcaaa gctgactcct gagcttttgt ccgtggaggc ctggggcggc    1740
gcgacctacg atgtggcgat gcgtttcctc tttgaggatc cgtgggacag gctcgacgag    1800
ctgcgcgagg cgatgccgaa tgtaaacatt cagatgctgc ttcgcggccg caacaccgtg    1860
ggatacaccc cgtacccaga ctccgtctgc cgcgcgtttg ttaaggaagc tgccagctcc    1920
ggcgtggaca tcttccgcat cttcgacgcg cttaacgacg tctcccagat gcgtccagca    1980
atcgacgcag tcctggagac caacaccgcg gtagccgagg tggctatggc ttattctggt    2040
gatctctctg atccaaatga aaagctctac accctggatt actacctaaa gatggcagag    2100
gagatcgtca agtctggcgc tcacatcttg gccattaagg atatggctgg tctgcttcgc    2160
ccagctgcgg taaccaagct ggtcaccgca ctgcgccgtg aattcgatct gccagtgcac    2220
gtgcacaccc acgacactgc gggtggccag ctggcaacct actttgctgc agctcaagct    2280
ggtgcagatg ctgttgacgg tgcttccgca ccactgtctg gcaccacctc ccagccatcc    2340
ctgtctgcca ttgttgctgc attcgcgcac acccgtcgcg ataccggttt gagcctcgag    2400
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgcgg atcgtttcga actcatcgaa    2580
gacaactacg cagccgttaa tgagatgctg ggacgcccaa ccaaggtcac cccatcctcc    2640
aaggttgttg gcgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgatccgcc tgccagatgt gcgcacccca    3060
ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg gaaggtggcg acttgatcgt cgtcgtttcc    3420
taa                                                                  3423
```